(12) United States Patent
Bertrand et al.

(10) Patent No.: US 8,383,068 B2
(45) Date of Patent: Feb. 26, 2013

(54) APPARATUS FOR PERFORMING AMPLICON RESCUE MULTIPLEX PCR

(75) Inventors: Jeff Bertrand, Hazel Green, AL (US); Jian Han, Huntsville, AL (US)

(73) Assignee: iCubate, Inc., Huntsville, AL (US)

( * ) Notice: Subject to any disclaimer, the term of this patent is extended or adjusted under 35 U.S.C. 154(b) by 180 days.

(21) Appl. No.: 12/780,698

(22) Filed: May 14, 2010

(65) Prior Publication Data
US 2010/0291668 A1 Nov. 18, 2010

Related U.S. Application Data (60) Provisional application No. 61/178,111, filed on May 14, 2009.

(51) Int. Cl.
*C12M 1/34* (2006.01)
*C12M 1/00* (2006.01)
(52) U.S. Cl. ........... 422/554; 422/547; 422/500; 422/50
(58) Field of Classification Search .................. 422/554, 422/547, 500, 50
See application file for complete search history.

(56) References Cited

U.S. PATENT DOCUMENTS

| 5,658,531 | A | * | 8/1997 | Cope et al. .................... 422/410 |
| 5,955,736 | A | | 9/1999 | Robinson et al. |
| 2002/0142454 | A1 | | 10/2002 | Cracauer et al. |
| 2004/0262162 | A1 | | 12/2004 | Roach et al. |
| 2005/0089444 | A1 | * | 4/2005 | Justin et al. ..................... 422/63 |
| 2005/0158787 | A1 | | 7/2005 | Hongo et al. |

* cited by examiner

*Primary Examiner* — Christine T Mui
(74) *Attorney, Agent, or Firm* — Maynard Cooper & Gale, P.C.; Jon E. Holland (57) ABSTRACT

A cassette for performing multiplex PCR is described. The cassette allows for the automated amplification and detection of multiple nucleic acid targets while limiting contamination. The device facilitates a two-amplification, two-primer PCR protocol which results in highly specific, highly sensitive and semi-quantitative amplification of multiple nucleic acid targets. The cassette contains a cavity, a base with a plurality of chambers, a movable pipette for the transfer of reagents and a detection area. The cassettes are single use, disposable devices which may be loaded with reagents needed for the detection of multiple targets. The cassettes may be used in a hospital or clinical setting to quickly screen clinical samples and detect the presence of infectious agents.

17 Claims, 10 Drawing Sheets

APPARATUS FOR PERFORMING AMPLICON RESCUE MULTIPLEX PCR

CROSS-REFERENCE TO RELATED APPLICATIONS

This application claims priority to U.S. Provisional Patent Application No. 61/178,111 filed on May 14, 2009, the entire contents of which are incorporated herein by reference.

FIELD OF THE DISCLOSURE

The disclosure relates generally to machines and methods for amplifying nucleic acids. More specifically, the disclosure relates to machines and methods for enabling the amplification of multiple nucleic acid sequences by polymerase chain reaction.

BACKGROUND OF THE DISCLOSURE

The development of the polymerase chain reaction (PCR) enabled the use of DNA amplification for a variety of uses, including molecular diagnostic testing. The use of PCR for molecular differential diagnostic (MDD) assays presents several challenges, however. PCR utilizes specific primers or primer sets, temperature conditions, and enzymes. PCR reactions may easily be contaminated, primer binding may require different conditions for different primers, primers should be specific for a target sequence in order to amplify only that target sequence, etc. This has made it even more difficult to amplify multiple sequences from a single sample.

Diagnostic testing of clinical samples to find one or more causative disease agents has, in the past, required that microorganisms be isolated and cultured. However, this may take days while in many cases a diagnosis must be acted upon within hours if the patient's life is to be saved. Identification of one or more disease-causing agents within a clinical sample within a matter of hours is the goal, and methods have been developed to better accomplish that goal. For example, multiplex PCR methods have been developed to amplify multiple nucleic acids within a sample in order to produce enough DNA/RNA to enable detection and identification of multiple organisms. Multiplex PCR has disadvantages, however. For example, amplification of each target in a multiplex PCR reaction requires its own optimal reaction conditions, so increasing the number of targets requires that the reaction conditions for each individual target be less than optimal. Furthermore, multiple sets of high-concentration primers in a system often generate primer dimers or give non-specific background amplification. This lack of specificity also requires the additional steps of post-PCR clean-up and multiple post-hybridization washes. Crowded primers reduce the amplification efficiency by requiring the available enzymes and consuming substrates. Differences in amplification efficiency may lead to significant discrepancies in amplicon yields. For example, some loci may amplify very efficiently, while others amplify very inefficiently or fail to amplify at all. This potential for uneven amplification also makes it difficult to impossible to accurately perform end-point quantitative analysis.

A method that has overcome many of the multiplex PCR challenges is target-enriched multiplex PCR (tem-PCR). In a tem-PCR procedure, nested gene-specific primers are used at very low concentrations to enrich the targets during the initial PCR cycling. Later, SuperPrimers are used to amplify all the targets. In this process, nested primers increase compatibility among loci and decrease background amplification, as well as increasing the range of optimal conditions under which primers can bind. An obvious benefit of the tem-PCR method is its ease of use. The entire reaction is performed in one tube, no additional rounds of PCR are required, and it does not require specialized instruments but may instead be performed using regular thermal cyclers.

Multiplex and tem-PCR techniques offer the ability to perform multiple assays at a time on a single sample, but at present they must do so by sacrificing much of the sensitivity that can be achieved by single amplification reactions using a single set of target-specific primers. It is still desirable to improve on the technology in order to provide diagnostic tests with greater sensitivity and shorter diagnostic time. It is also desirable to integrate the amplification and detection steps so that open-tube hybridization steps can be eliminated to reduce false positives caused by carry-over contamination by PCR products.

SUMMARY

The disclosure relates to a self-contained cassette for performing amplicon rescue multiplex PCR amplification (ARM-PCR) of DNA and/or RNA and detection of the DNA amplicons obtained therefrom. Amplification and detection may be successfully performed for multiple different organisms from a sample which may contain one or multiple infectious agents, such as a variety of bacteria, viruses, and fungi, for example. The cassette comprises a substantially closed environment surrounded on all sides by at least one barrier material that protects the internal contents of the cassette from the external environment thereby forming a cavity, a cassette pipette which can be moved both vertically and horizontally within the cassette under the control of an external base unit, at least one reagent for at least one PCR amplification reaction, at least one reagent chamber for containing the at least one reagent, and at least one detection chamber containing at least one microarray for detection of DNA produced by PCR amplification. Reagents may include appropriate primers necessary for the amplification of DNA from a specific variety of microorganisms, and one or more corresponding microarray(s) may be paired with the primers included in the cassette to provide a detection panel that is effective for detection of agents causing respiratory illness, gastrointestinal illness, sexually-transmitted disease, or other system-specific disease, for example.

In some aspects, the disclosure comprises a cassette comprising a cassette pipette which can be moved both vertically and horizontally within the cassette under the control of an external base unit; at least one pair of target-specific primers for a first amplification reaction performed with the cassette to amplify DNA/RNA to produce at least one amplicon in a target-specific manner; at least one pair of target-independent primers for a second amplification reaction performed within the cassette to amplify DNA of the at least one amplicon in a target-independent manner to produce at least one amplicon from at least one pair of common primers; and at least one detection means for detecting and identifying the amplicons. The disclosure also provides, in certain aspects, kits comprising at least one cassette of the disclosure, at least one pair of target-specific primers, at least one common primer, and at least one microarray, the at least one pair of target-specific primers and at least one microarray chosen to provide for amplification and detection of a desired set of target agents. In some aspects, for example, a desired set of target agents may include bacteria and/or viruses which are generally known to cause respiratory illness, bacteria and/or viruses which are generally known to cause gastrointestinal illness, bacteria which are generally associated with sepsis, etc.

DETAILED DESCRIPTION

The disclosure relates to a cassette for performing PCR amplification of DNA and/or RNA obtained from a clinical specimen. Such a specimen may contain one or multiple infectious agents such as, for example, bacteria, viruses, and fungi. The cassette also comprises at least one detection means for detecting and identifying the resulting DNA produced by the PCR amplification reactions performed within the cassette. The cassette enables the performance of amplicon-rescue multiplex PCR (ARM-PCR), a technique that has been described previously in U.S. patent application Ser. No. 12/418,532 and PCT application number PCT/US09/39552. To provide the necessary reagents for ARM-PCR, the cassette also comprises appropriate nested, target-specific primers for a first, target-specific amplification reaction and common primers for a second, target-independent amplification reaction. These amplification reactions may be performed in the same or in different reagent chambers. It is intended that the terms "consist of" and/or "consist essentially of" may be substituted for the term "comprising" as used herein.

Briefly, ARM-PCR is a method for producing detectable amounts of target polynucleotides from a specimen such as a clinical, environmental, or food sample, the method comprising amplifying, in a first amplification reaction using nested primers, one or more target polynucleotides to produce amplicons, at least a portion of the nested primers comprising additional nucleotides to incorporate into a resulting amplicon a binding site for at least one communal primer; rescuing the amplicons of the first amplification reaction from one or more unused primers of the first amplification reaction; and amplifying, in a second amplification using common primers, amplicons of the first amplification reaction having at least one binding site for a common primer. The cassette comprises a cassette pipette which can be moved both vertically and horizontally within the cassette during the amplification and detection protocols and which can be manipulated by an external base unit to aspirate and/or release fluids in order to move reagents to and from the cassette's reagent chambers. The cassette also comprises the necessary reagents for DNA extraction and PCR amplification reactions (e.g., enzymes, buffers, dNTPs, etc.) these reagents being contained within one or more (i.e., at least one) reagent chamber(s), and at least one detection chamber containing at least one microarray for detection of DNA amplified during the reactions. In aspects of the disclosure, the detection chamber will contain at least one DNA microarray.

Reagent chambers may be arranged in any pattern—e.g., linear, circular, etc., and at least one reagent chamber may also serve as at least one reaction chamber where the polymerase chain reaction amplifications are performed. Reagent chambers may be of equal or similar depth, but may also be of varying depths so that one reagent chamber may be deeper than another. This may particularly be the case where a reagent chamber serves as a reaction chamber. Reagents may include, and preferably will include, appropriate primers necessary for amplification of DNA from a specific variety of microorganisms, and one or more corresponding microarray(s) may be paired with the primers included in the cassette. For example, a cassette may contain primers and one or more microarray(s) specific for several microorganisms that are known to be associated with respiratory infections, so that a clinical sample taken from a patient who presents with symptoms of a respiratory infection may be tested for the presence of any one of the microorganisms using the one single cassette.

A cassette is insertable into a base machine ("base unit") that operably interfaces with the cassette to provide the necessary movement of a series of parts designed to provide up-and-down vertical movement, horizontal back-and-forth movement, and fluid handling by a cassette pipette which operates within the confines of the area bounded by the top, bottom, ends, and sides of the cassette, these parts being referred to as a cam bar, a lead screw, and a pipette pump assembly, respectively. It may also be desirable to provide a mechanism allowing the movement of the cassette pipette in any direction in the x-y-z plane, or to allow for circular/rotary movement throughout the enclosed cassette.

Referring now to the figures, the cassette pipette 20 is operably connected to a rotatable cam bar 16 so that rotation of the bar 16 results in a corresponding movement of the pipette 20 upward and/or downward in a vertical direction. A pipette holder 28 supports and guides the up and down movement of the cassette pipette 20, the pipette holder 28 being supported by and slidably positioned within the cassette 1. A lead screw 24 is positioned within the cassette 1 is operably connected to the pipette holder 28 so that rotation of the lead screw 24 produces a corresponding lateral movement of the pipette holder 28, thereby forming a means for positioning the pipette 20 above the appropriate fluid well 49 at each stage of the amplification/detection process.

The base 4 of the cassette 1 comprises at least one sample chamber 42, and at least one reagent chamber 49 for containment of reagents (not shown). Reagent chamber 49 may be of identical, similar, or dissimilar size, shape, and depth and may be arranged in a variety of positions in the base 4 of the cassette 1. Desired reagents (not shown) are placed within the appropriate reagent chambers 49 so that the cassette pipette 20 may gather the reagents needed for the extraction and the two-step, two-primer-set amplification as the process proceeds within the cassette 1. Reagent chambers 49 may be pre-loaded and preferably sealed prior to shipping, with the sealing material comprising a material that will remain in place during shipping and storage but be readily punctured by the force of downward motion of the cassette pipette in order to open the reagent chamber 49 to allow retrieval of the contents using the cassette pipette 20. One such material that is appropriate for sealing the reagent chamber, either individually, or as a group, is a thin sheet of aluminum foil (not shown). In aspects of the disclosure, among the reagent chambers are two reagent chambers which will contain target-specific primers and common, non-target-specific primers, respectively. These primers are used for the first and second amplification reactions, the first amplification being target-specific to provide amplicons representing the DNA and/or RNA of the variety of targets which may be found within the sample, and the second amplification being primed by common primers to allow semi-quantitative non-specific amplification of the amplicons of the first amplification. In this two-step process, the first amplification being primed by target-specific primers provides specificity, while the second amplification being primed by common primers increases sensitivity.

Also provided in the base 4 of the cassette 1 is a detection chamber 48 containing a microarray 44 for detection of the DNA which has been amplified during the two-step ARM-PCR protocol. Microarrays are known in the art and methods for preparing target-specific microarrays are well-known to those of skill in the art.

The figures illustrate side views of a cassette of the disclosure, having a top 2, base 4, first end 6, second end 7, a first side 11, a second side 13, fill port cap 12, fill port 14, cam bar 16, O-ring seals 91, 92, cam bar actuator 18, cassette pipette 20, pipette spring 22, lead screw 24, pipette holder 28, a pipette pump assembly 41 comprising a push rod 8, cylinder 32, plunger 34, tubing 36, spring 38, and an optional cassette vent (not shown). The base 4 comprises a sample chamber 42 and a series of reagent chambers 49 for holding the various reagents and fluids necessary for the performance of PCR reactions. By way of example, in some aspects of the disclosure a cassette 1 of the disclosure may comprise a series of reagent chambers 49 so that a first reagent chamber containing PCR 1 reagents (primers, buffers, etc. for the first PCR reaction using the nested primers), a second reagent chamber containing mineral oil for layering the top of the PCR reaction mix, a third reagent chamber containing a capture probe, a fourth reagent chamber containing magnetic beads, a fifth reagent chamber comprising a waste chamber, a sixth reagent chamber containing PCR2 reagents (primers, buffers, etc. for the second PCR reaction using at least one communal primer), a seventh reagent chamber containing hybridization fluid, and an eighth reagent chamber containing washing fluid. At least one reagent chamber may also perform the function of a detection chamber 48, comprising at least one microarray 44. Furthermore, the detection chamber 48 may also contain at least one detector door (not shown) having a detector door latch (not shown) and a door spring (not shown) in order to prevent the microarray 44 from being touched or contaminated by a user (not shown). A chamber cover 50, can be placed over the base 4, and hence the reagent chamber(s) 49.

A fill port 14 in the top of the cassette allows a user to insert a pipette (not shown) from the environment outside the cassette into a sample chamber 42. A clear plastic window (not shown) may be formed in the cassette 1 to be position so that it allows the user to see the user's pipette tip (not shown) as it is being inserted into the cassette 1 to deposit the sample (not shown) to be analyzed. In one embodiment, the clear viewing window is constructed to withstand the temperature extremes of the cassette. Alternatively, the entire enclosure of the cassette 1 may be formed from transparent or translucent plastics allowing the user to visualize the inner workings of the cassette.

In one embodiment, the fill port cap 12 located on top of the cassette will be a one-time operation cap, meaning that once the cap is sealed after sample insertion it cannot be reopened, thereby maintaining the integrity of the seal and keeping the system closed. In another embodiment, a sliding door 10 may be utilized such that once the sample (not shown) is introduced into the cassette 1, the sliding door 10 may be slid in the direction of arrow 72 (FIG. 3) and locked into place. The sliding door 10 may be locked into place by virtue of a tab (not shown) formed into the sliding door 10 that fits within a channel (not shown) molded into the top 2 which allows movement in one direction, such that once the sliding door 10 passes a certain point, the channel (not shown) ends thereby preventing the sliding door 10 from traveling back towards its original position. The fill port cap 12 seals the fill port 14. In one embodiment, the fill port 14 has a minimum inside diameter of 0.3 inches to allow for insertion of a 20 µl pipette through the fill port 14 and into the sample chamber 42. The fill port 14 may be other sizes in other embodiments of the present disclosure.

Figure 2A:
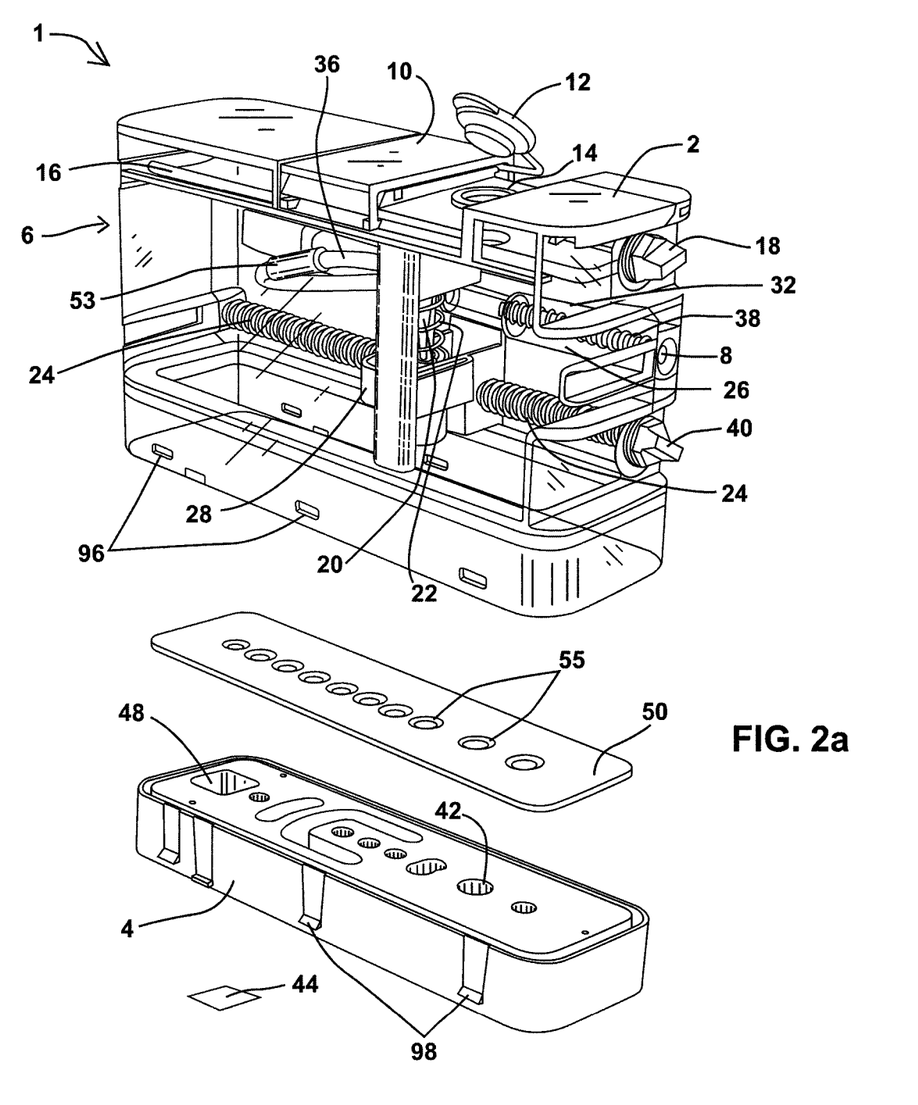
FIG. 2a is an exploded view of the cassette of FIG. 1.
Figure 2B:
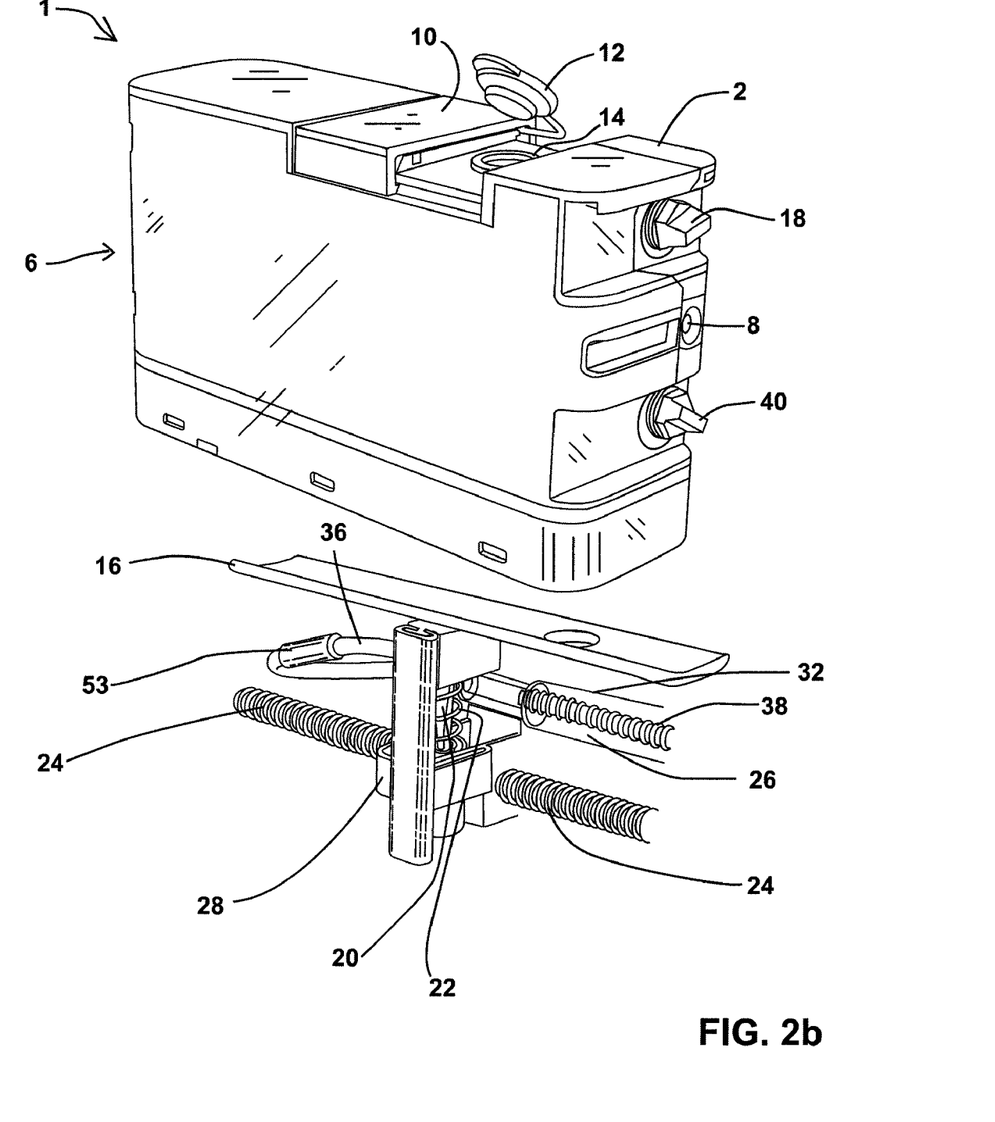
FIG. 2b is another exploded view of the cassette of FIG. 1.
Figure 2C:
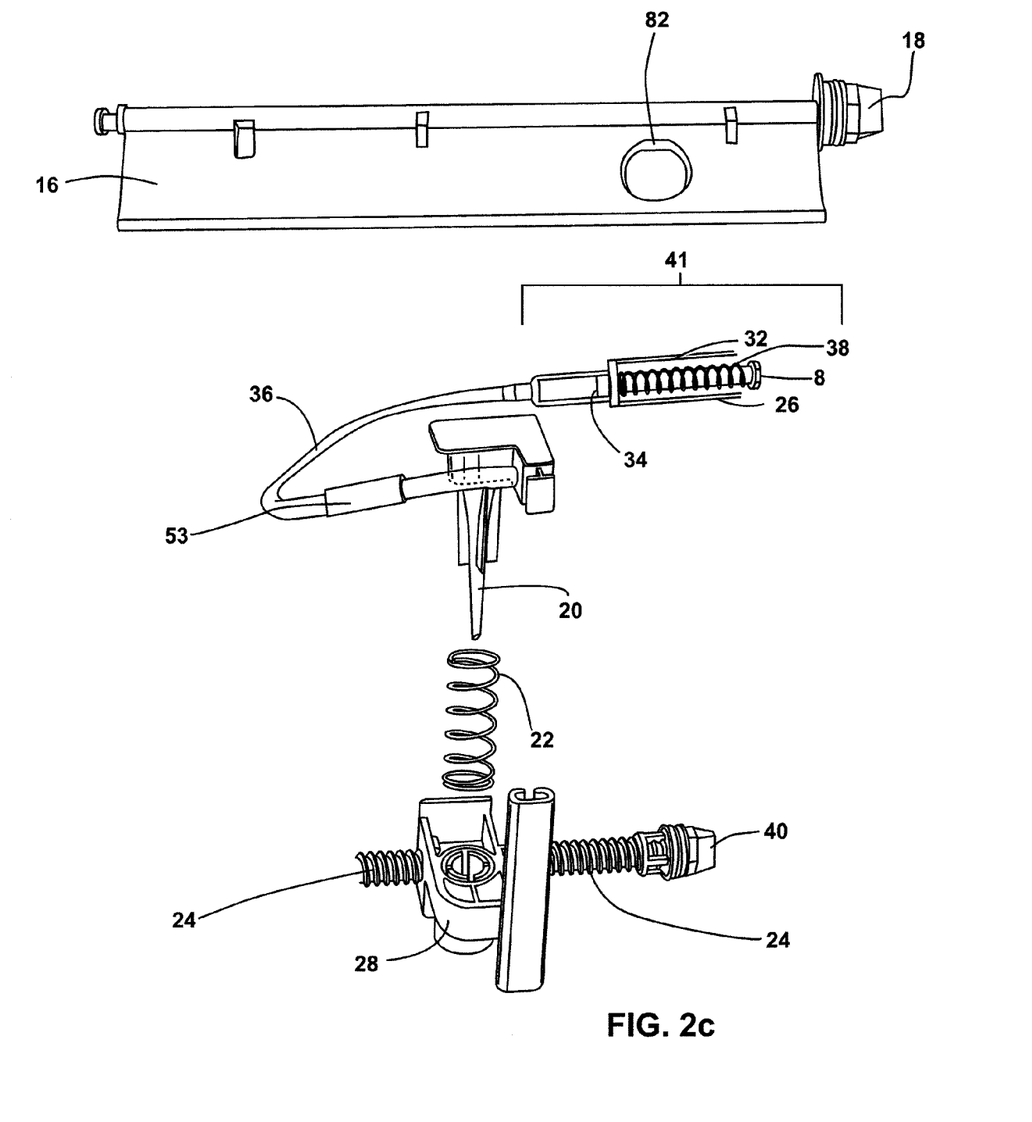
FIG. 2c is another exploded view of the cassette of FIG. 1.
Figures 4A, 4B:
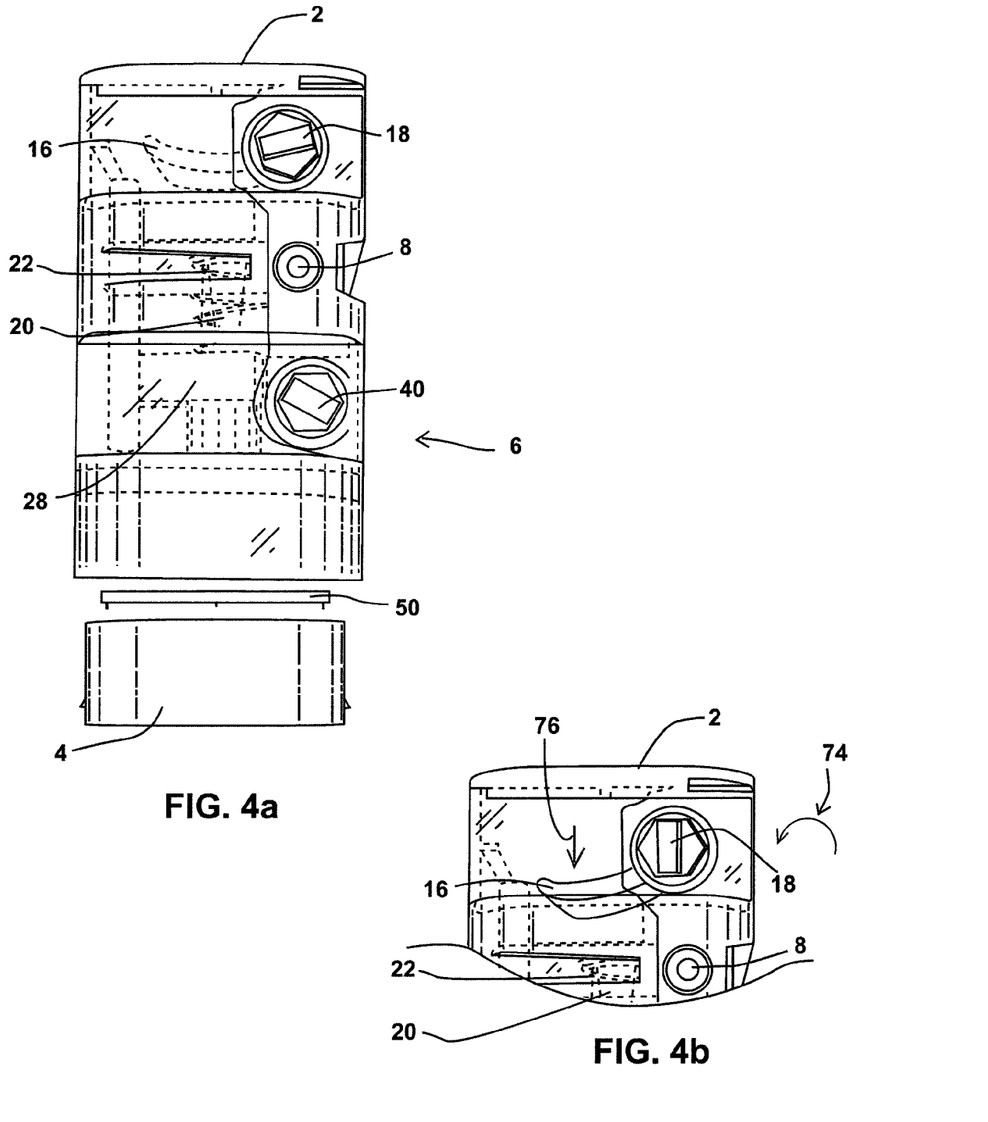
FIG. 4a is a front exploded view of the cassette of FIG. 1.
FIG. 4b is a front cut-out view of the cassette of FIG. 1.
Figure 5:
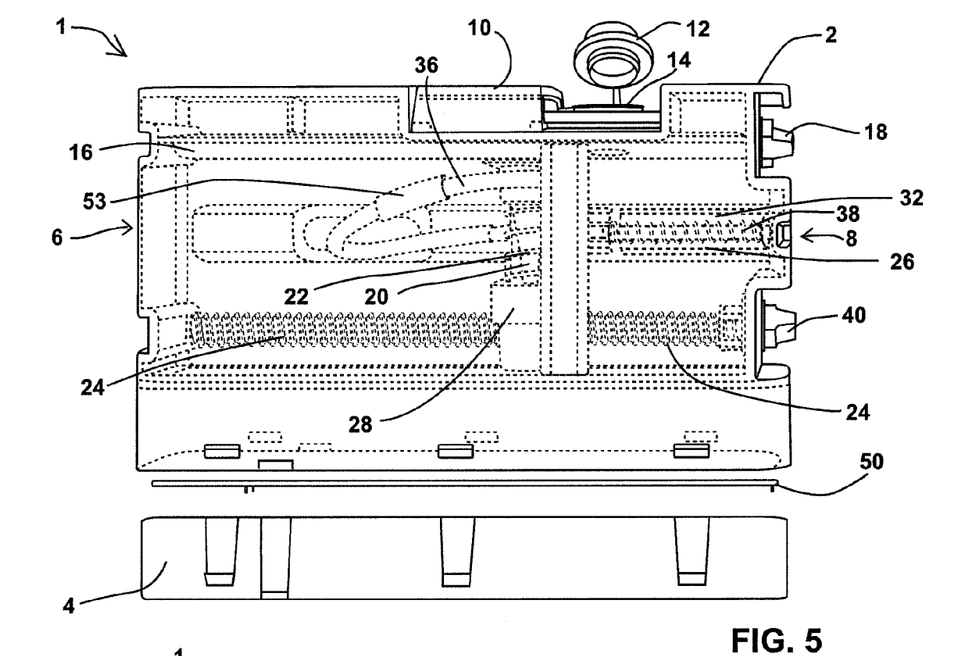
FIG. 5 is an exploded left side view of the cassette of FIG. 1.
Figure 6:
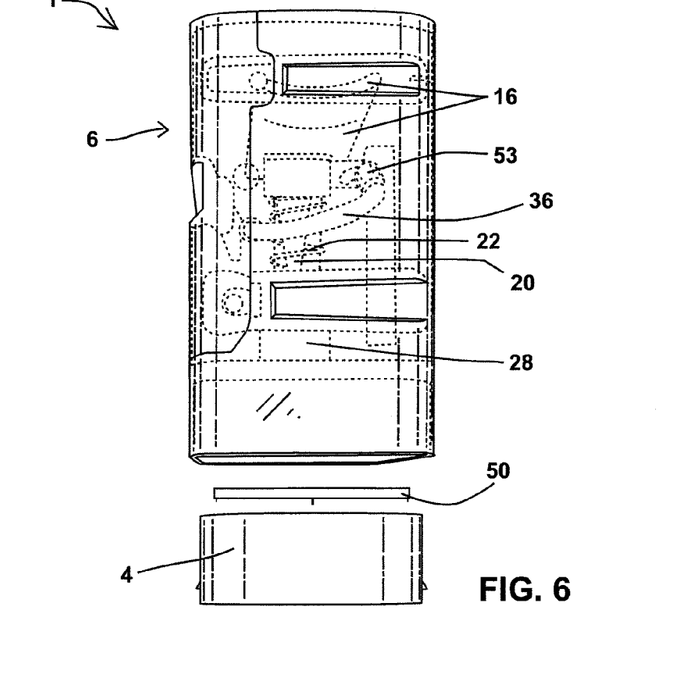
FIG. 6 is an exploded back view of the cassette of FIG. 1.
Figure 7:
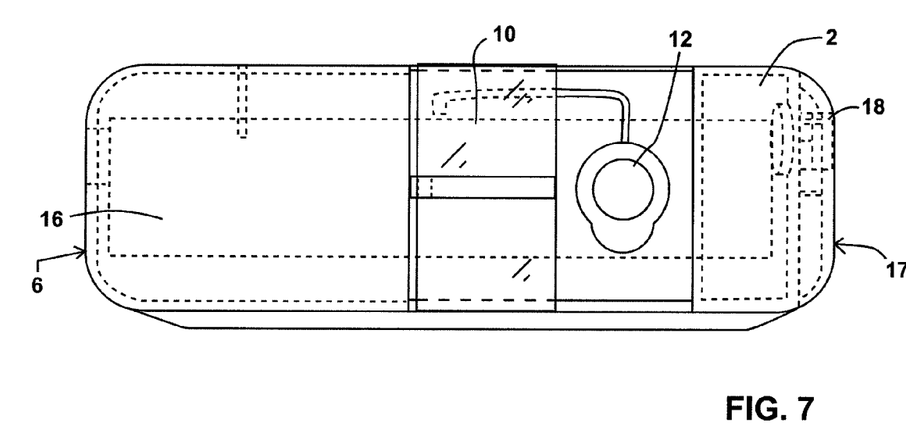
FIG. 7 is a top view of the cassette of FIG. 1.
Figure 8:
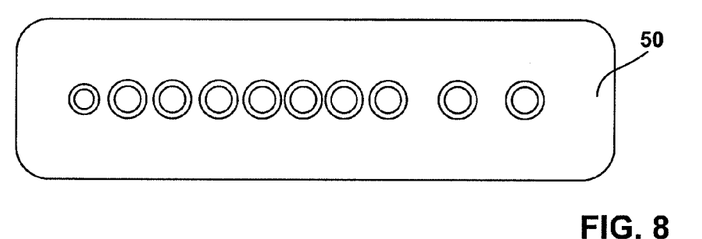
FIG. 8 is a top view of a chamber cover of the cassette of FIG. 1.
Figure 9:
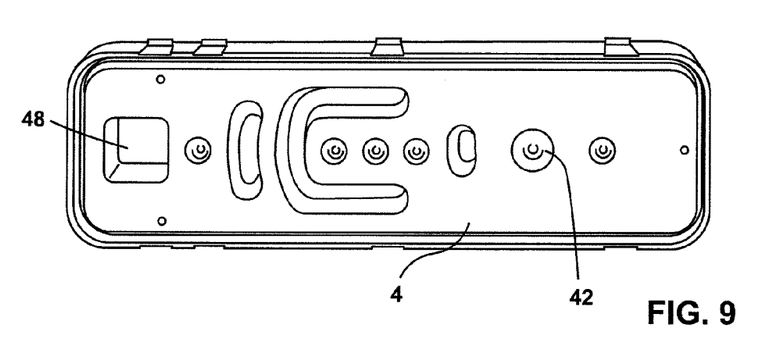
FIG. 9 is a top view of the base of cassette of FIG. 1.
Figure 10:
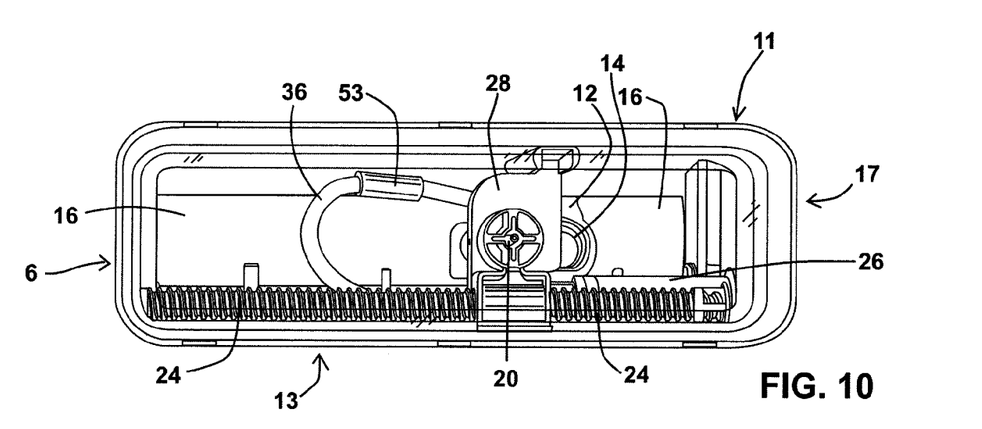
FIG. 10 is a bottom view of the cassette of FIG. 1 with the base and chamber cover removed.
Figure 11:
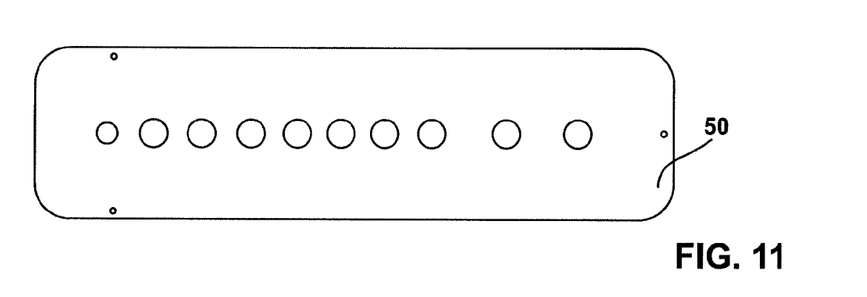
FIG. 11 is a bottom view of the chamber cover.
Figure 12:
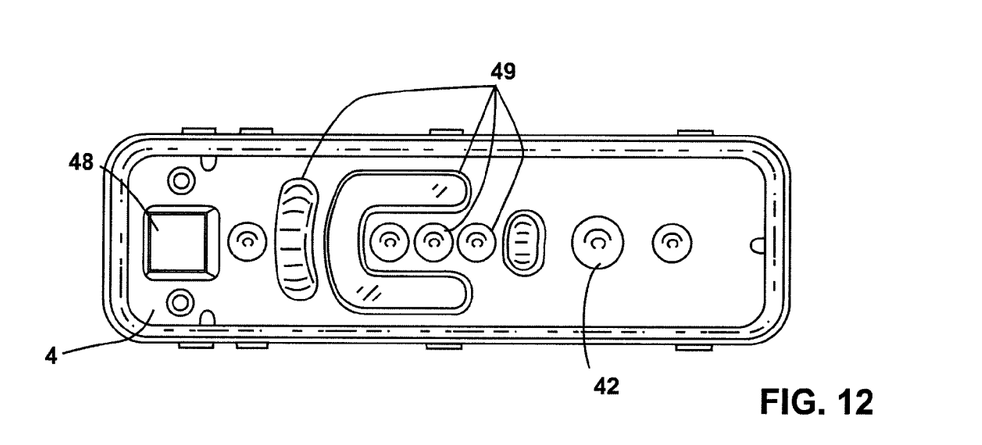
FIG. 12 is a bottom view of the base of the cassette of FIG. 1.
Figure 13A:
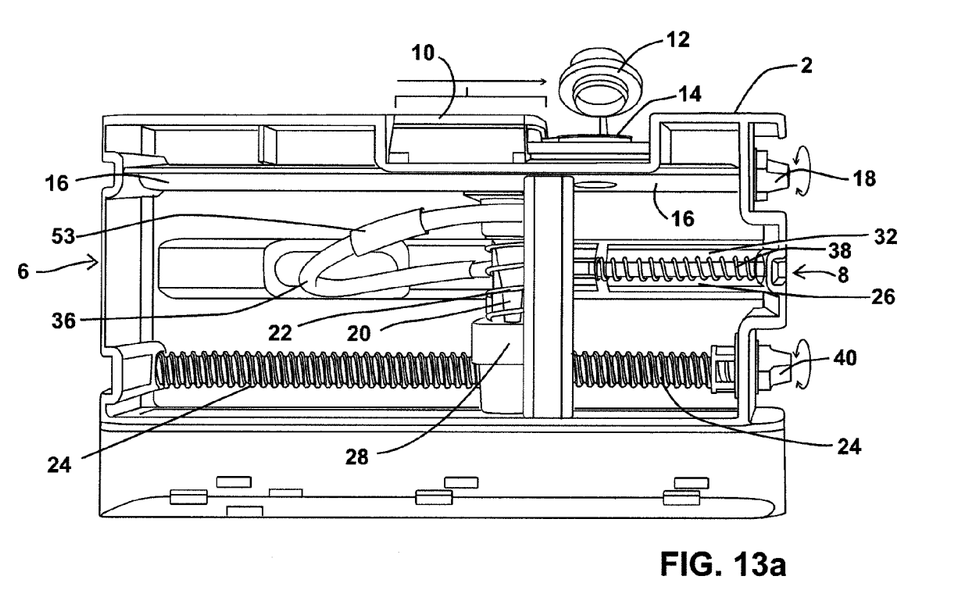
FIG. 13a is a left side view of the top portion of the cassette of FIG. 1.
Figure 13B:
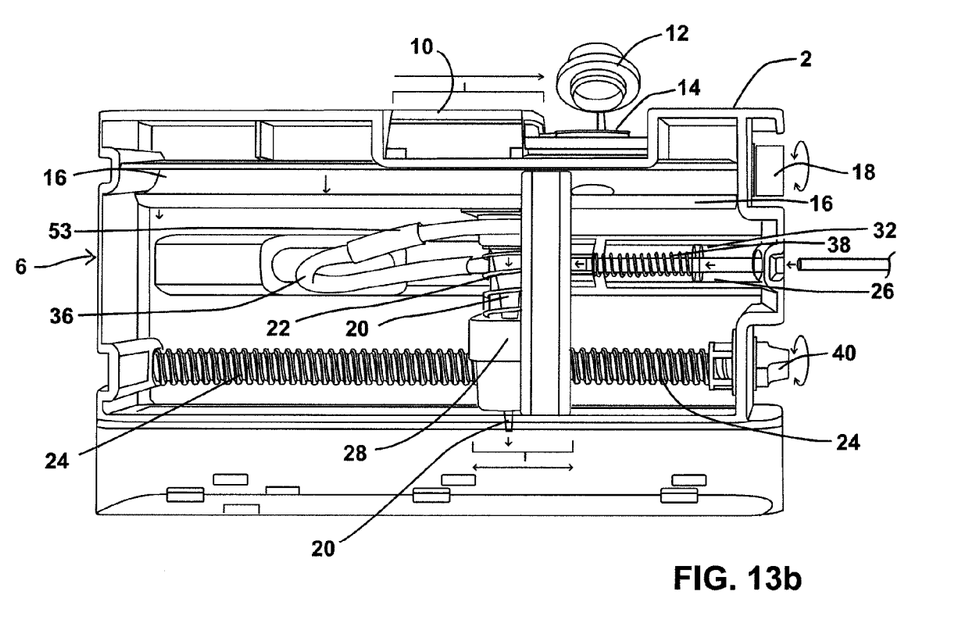
FIG. 13b is the left side view of the top portion of the cassette as shown in FIG. 13a showing a spring in an actuated position.

Movement of the cassette pipette 20 in a vertical, up-and-down manner, is provided by a cam bar 16 which is connected to an external base unit (not shown) by means of a mechanical interface 18 immovably coupled to the cam bar 16, allowing movement of the cassette pipette 20 to be controlled by the base unit (not shown). In one embodiment, the mechanical interface 18 is a knob, however, other mechanical interfaces may be used in other embodiments. As shown in FIG. 4b, rotation of the cam bar 16 from its home position (shown in FIG. 4a) in the counterclockwise direction indicated by arrow 74 causes the cam bar 16 to travel in the direction indicated by arrow 76 and press down on the top of the pipette 20, pushing the pipette 20 down and into the sample chamber 42 or one of the reagent chambers 49. When the cam bar 16 is rotated back to its home position, a pipette spring 22 operably connected between both the cam bar 16 and the cassette pipette 20 removes the pipette 20 from the sample chamber 42 or reagent chamber 49 and returns it to its home position. When in the home position, the cam bar 16 contains an opening 82 (FIG. 2c) to allow for sample insertion through the fill port 14 and into the sample chamber 42 without interfering with the user's use of an appropriately-sized pipette (not shown). The maximum angle of rotation of the cam bar 16 and the mechanical interface 18 places the cassette pipette 20 tip at the bottom of a reagent chamber 49 (or sample chamber 42) and the minimum angle of rotation places the cam bar 16 in the home position, with the cassette pipette 20 tip positioned above the top of a reagent chamber 49 (or sample chamber 42). In this position, as the cassette pipette 20 travels laterally back and forth in the cassette 1 the cassette pipette 20 should not come into contact with any internal surface of the cassette 1. A pipette spring 22 is generally a compression spring with a spring constant sufficient to allow the pipette to follow the motion of the cam bar 16, while remaining in contact with it at all times. The spring 22 may be formed of metal and/or plastic. In one embodiment, it's the material of the spring 22 allows for a slight misalignment between the pipette 20 tip and the reagent chamber 49 or sample chamber 42 without interfering with the overall motion of the pipette 20.

Figure 3:
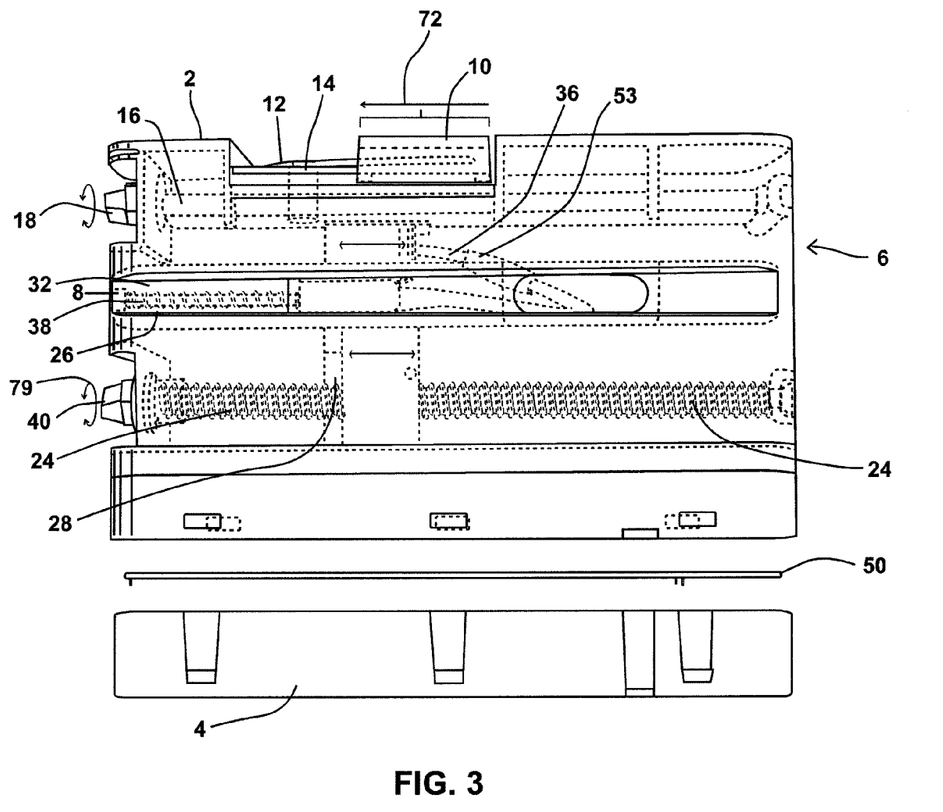
FIG. 3 is an exploded right side view of the cassette of FIG. 1.

The cassette pipette 20 is supported and held in position by a pipette holder 28. The pipette holder 28 is slidably received along the length of the cassette 1. The pipette holder 28 may be retained along the same lateral plane of the cassette 1 by a first and second guiderail (not shown) which can be molded into the sides 11, 13 of the cassette 1. Such guiderails may be positioned vertically parallel to each other and horizontally positioned between a first end 6 and a second end 17 of the cassette. The pipette holder 28 is operably connected to the lead screw 24. The lead screw 24 is threadedly received into the pipette holder 28 by means of a male-female thread pairing between the lead screw 24 and the pipette holder 28. A mechanical interface 40 is immovably connected to the lead screw 24 allowing both clockwise and counterclockwise rotation as indicated by arrow 79 (FIG. 3). Rotation of the mechanical interface 40 rotates the lead screw 24, the pipette holder 28 follows the thread of the lead screw 24 and is moved laterally along the lead screw 24 along the length of the cassette 1. Reversing the direction of rotation of the lead screw 24 causes a corresponding reversal of motion of the pipette holder 28. By controlling the number of rotations and direction of rotation of the lead screw 28, the pipette can be accurately positioned above any one of the reagent chamber 49 or sample chamber 42 located in the base 4. In one embodiment, the mechanical interface 40 is a knob, however, other types of mechanical interfaces may be used in other embodiments.

In one embodiment, the lead screw 24 is constructed from plastic and/or metal. However, the lead screw 24 may be made of other materials or types of materials in other embodiments. The thread pitch of the lead screw 24 should be chosen to optimize the speed of translational motion and position accuracy of the pipette holder 28. In one embodiment, the lead screw 24 is not flexible, bendable, or bindable in a way that would impede its ability to produce horizontal movement of the pipette holder 28. In one embodiment, the lead screw 24 has an overall length that will allow the pipette to reach all reagent chambers 49 and sample chambers 42 located in the base 4. A low friction o-ring seal 91 around the cassette opening through which the lead screw 24 engages the cassette 1 maintains the relatively contaminant-free environment within the cassette 1. In one embodiment, the lead screw 24 is constructed to withstand the temperature extremes of the cassette, keeping in mind that the cassette will be used for DNA/RNA amplification using thermocyclic reaction conditions.

The location of the pipette holder 28 within the chamber may be detected optically, magnetically, or mathematically by virtue of the number of rotations of the lead screw 24. If optically, the sides 11, 13 of the cassette 1 will need to be sufficiently translucent or transparent to allow for detection by standard optical sensors known in the art. If the location of the pipette holder 28 is to be detected magnetically, a magnet (not shown) imbedded in the back of the pipette holder 28 may be detected by a series of Hall effect devices located in a base unit, the cassette 1 being inserted into the base unit (not shown) for performance of the desired chemical reactions and detection procedure. As the pipette holder 28 and its attached magnet (not shown) moves along the guiderails (not shown), a Hall effect device (not shown) located in the base unit (not shown) but external to the cassette 1 is aligned with each reagent chamber 49 location to detect the presence or the absence of the magnetic field. When the pipette 20 becomes vertically aligned with a reagent chamber 49 or sample chamber 42, the specific Hall effect device (not shown) for that location will detect the presence of the magnetic field. In one embodiment, other Hall effect devices corresponding to the other reagent chambers 49 do not detect the magnetic field and indicate the absence of a magnetic field. Any output signals (not shown) of the Hall effect devices are detected by the corresponding detectors located in the base unit, confirming the location of the cassette pipette 20.

The cassette pipette 20 is fluidly connected to a pipette pump assembly 41 comprising a push rod 8, cylinder 32, plunger 34, tubing 36, and spring 38. In one embodiment, the tubing 36 is flexible and, in one embodiment, the tubing 36 comprises a type of tubing 36 referred to as "flat tubing." The tubing also includes a spiral wrap 53 which prevents the tubing 36 from interfering with the sides 11, 13 of the cassette 1 as the pipette holder 28 travels throughout the cassette 1. The pipette pump assembly 41 is operably connected to a base unit (not shown) so that a movable part (not shown) of the base unit (not shown) compresses the push rod 8 and plunger 34 into the cylinder 32 of the pipette pump assembly 41 and the pressure difference produced by this compression is transferred through the tubing 36 into the pipette 20, with movement of the push rod 8 and plunger 34 within the cylinder 32 producing either a suitable vacuum with which to draw fluid from a reagent chamber 49 or sample chamber 42 into the cassette pipette 20 or a suitable force of air to expel the contents of the cassette pipette 20 into a reaction chamber 49 or detection chamber 48. Accordingly, in such an embodiment, the pipette pump assembly 41 from the plunger 34 to the tubing 36 to the tip of the pipette 20 remains in fluid communication.

The push rod side of the cylinder 32 and plunger 34 should be open to the external air of the cassette 1, preventing pressurization of the backside of the plunger. In one embodiment, the internal volume of the cylinder 32 is sufficient to produce the motion of the pipette fluid volume. As the plunger 34 is moved inside the cylinder 32 to change its volume air space under the force of the push rod 8, air in the cylinder is displaced by the plunger 34, causing an air pressure change that is translated to the pipette 20 through the tubing 36. Thus, the plunger 34 therefore forms a low friction, substantially airtight seal with the inside cylinder 32 wall. This seal is maintained when there is an increase in air pressure or a decrease in air pressure in the cylinder, and is maintained during the motion of the plunger 34 so it can accurately control the amount of fluid moved by the pipette. The internal motion of the plunger 34 is sufficient to allow for the required motion of the pipette fluid volume.

The tubing 36 is fluidly connected to the plunger 34, so that air moves within the tubing in correlation to the action of the plunger 34. The tubing 36 has an internal volume or inside diameter sufficient to transfer the change in pressure in the cylinder 32 to the pipette 20 in an optimal amount of time. The use of flat tubing (not shown) will control its motion as the pipette 20 moves back and forth and up and down, as the tubing does not interfere with the motion of the pipette in any way. In one embodiment, the tubing 36 lies against the sidewall of the enclosure and moves freely with the cassette pipette 20 without hindering the motion of the cassette pipette 20.

A spring 38 forming part of the pipette pump assembly 41 lies between the push rod 8 and the second end 17 of the cassette 1, causing the push rod 8 to return to its home position when the force coming from the base unit (not shown) is removed. In one embodiment, the spring 38 is a compression spring and formed of metal and/or plastic. The spring 38 may be formed of other materials or types of materials in other embodiments of the present disclosure.

The tip of the cassette pipette 20 has a sufficiently narrow circumference to easily enter a reagent chamber 49, detection chamber 48, or sample chamber 42 and reach the bottom of such chambers. In one embodiment, the cassette pipette tip will be formed of a design and material that will not become entangled with a seal which may be placed over the chambers as the pipette tip punctures the seal (not shown) or is removed from the chamber through the opening created by puncturing the seal (not shown). The interface between the cassette pipette 20 and the pipette holder 28 allows sufficient freedom of movement so that a small misalignment between the pipette 20 tip and the fluid well can be tolerated. In one embodiment, a 100 microliter pipette may be used in the cassette 1 as shown in the figures. However, it is well within the skill of one of skill in the art of biotechnology to modify the size of the reagent chamber(s) 49, the sample chamber 42, the detection chamber 48 and the volume of the reagents. Therefore, pipettes of other volumes may also be used in various embodiments of the disclosure. The overall volume of the pipette 20 is large enough so that at no time fluid can be drawn into the tubing 36 during the maximum stroke of the pipette pump assembly 41. In on embodiment, the cassette pipette 20 is constructed of plastic, and the cassette pipette 20 is formed of a material to withstand the temperature extremes of the cassette 1, as well as relatively inert to the chemicals and reagents used.

Figure 1:
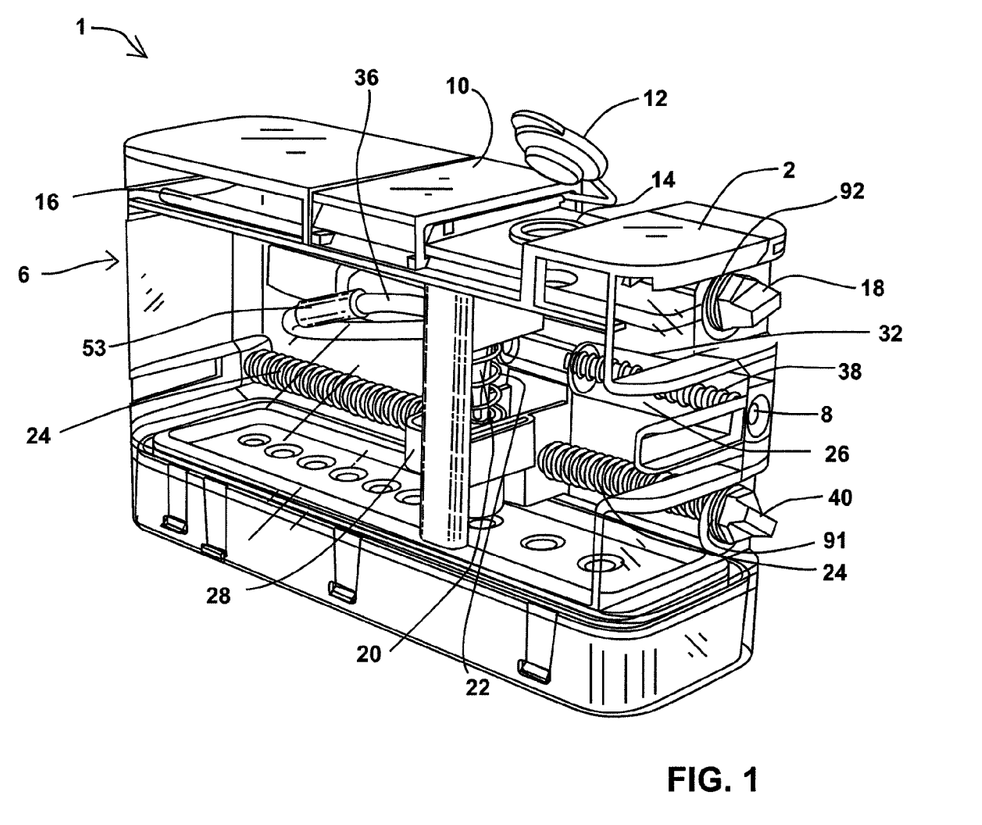
FIG. 1 is a front perspective view of a cassette and its component parts as provided by the disclosure.

The cassette base 4 is attached to the ends 6, 17, and sides 11, 13 of the cassette 1 via a substantially airtight seal. In one embodiment, the base 4 and the sides 11, 13 are connected via openings 96 in the sides 11, 13 and tabs 98 on the base 4 such that the tabs 98 and the openings 96 mate when the base 4 is attached as shown in FIG. 1. A small cassette vent (not shown) and filter (not shown), may be included along any location of the ends 6, 17 or sides 11, 13 to form a connection between the inside and outside of the cassette 1, allowing the internal pressure and external air pressure to be equalized in a controlled manner. The filter (not shown) may be dry or moist, inhibiting entry of contaminant particles while allowing equalization of air pressure between the cassette and the outside environment.

The cassette 1 of the present disclosure fits within a base unit (not shown) and is operably connecting therewith. The base unit (not shown) is programmed to coordinate the movements of and provide the motion for the cam bar 16, the lead screw 24, and the pipette pump assembly 41 in order to control the up-and-down and horizontal movements of the cassette pipette, as well as the removal of or addition of reagents into the appropriate reagent chambers 49 detection chamber 48 or sample chamber 42 by means of the cassette pipette 20. A reagent chamber 49 which may be used as an amplification reaction chamber interfaces with the base unit (not shown), coming into contact with the base unit heaters (not shown), when the cassette 1 is inserted into the base unit (not shown). The base unit heaters (thermocyclers) (not shown) cycle the temperatures to perform the desired PCR reaction(s).

The cassette base 4 further comprises at least one detection chamber 48 comprising one or more DNA microarray(s) 44 and reagents to perform the desired hybridization when the cassette pipette 20 deposits the reaction product (not shown) of the PCR2 reaction within the detector chamber 48. The detection chamber 48 is constructed so that a glass cover slip (not shown) with the detection microarray printed on it may be inserted prior to completion and shipment of the cassette 1. The glass cover slip (not shown) may be, for example, a 1 cm square slip of glass. In such an embodiment, the bottom edge of the chamber 48 is formed to accept the glass slip and the material used to form the detection chamber 48 is composed from a material that is fused to the glass cover slip. In one embodiment, the bottom of the detection chamber 48 is flat and parallel to the bottom surface of the base 4. The detection chamber 48 may be recessed into the base 4 to allow for the proper operation of a detector door if utilized. If utilized, the detector door (not shown) protect the bottom surface of the glass cover slip (not shown) or microarray 44 from damage during handling, such as that created by fingerprints, dust and scratches. The detector door (not shown) can slide out of the way once installed into the base unit machine (not shown). The detector door (not shown) is not triggered by normal handling, but easily triggered by connection with the base unit (not shown) upon insertion of the cassette 1 into the base unit (not shown).

The detection chamber 48 is positioned in coordination with the base unit (not shown) to contact the hybridization heater (not shown) and optical detector (not shown) of the base unit when the cassette 1 is inserted into the base unit (not shown). If a detector door (not shown) is utilized, insertion of the cassette 1 into the base unit (not shown) trips the detector door latch (not shown) of the detection chamber 48 and release the door (not shown) so that the door spring (not shown) pulls the detector door (not shown) out of the way—providing access to the glass cover slip (not shown) over the microarray 44 in the bottom of the detection chamber 48. Around the detection chamber 48 may be positioned a ring of material (not shown) removed around its periphery to create a thermal relief, so that the heat being transferred to the microarray 44 from the heater (not shown) is not lost to the base 4. In one embodiment, the reagent chambers 49 are designed so that a slight misalignment of the pipette 20 tip will still allow the pipette 20 to access fluids (not shown) inside the reagent chambers 49. Accordingly, in such an embodiment, the chamber cover 50 may be designed with tapered openings 55 to direct the pipette 20 into the reagent chambers 49 detection chamber 48 or sample chamber 42.

Detection may be performed by producing a digital image of the fluorescence of the DNA captured on the microarray 44 during hybridization. The microarray 44 is a grid of printed dots that contain special DNA capture probes selected to attach to a specific DNA target. By placing these capture probes into a known pattern, along with orientation markers and positive and negative control dots, the unknown DNA target can be detected and identified if it originates from one of the organisms represented on the microarray. The side of the glass cover slip (not shown) that contains the printed array is sealed to the detection chamber 48, and allowing the printed array (not shown) to come into contact with the hybridization fluids (not shown). The glass cover slip (not shown) should make an air and fluid seal to the bottom edge of the detection chamber 48, maintaining its integrity through the temperature extremes to which the cassette 1 is exposed during the PCR process. The material used to seal the glass slip (not shown) to the detection chamber 48 should be inert to the chemicals that are placed into the detection chamber 48. The microarray 44 is printed on the inside surface of a glass cover slip (not shown), so the excitation light source of the base unit is directed up through the bottom of the glass slip (not shown), exciting a fluorescent label on the DNA product. A digital camera (not shown) or photo multiplier tube (not shown) located beneath the external hybridization heater (not shown) in the base unit (not shown) captures the image of the fluorescent patterns on the microarray 44. The optical integrity of the glass cover slip (not shown) should be maintained throughout this process because the microarray 44 is made up of many printed dots only a few microns in diameter.

At least one of the reagent chambers 49 in the base 4 may form a PCR reaction chamber for performing the desired PCR1 and PCR2 reactions. Such a reaction chamber may be constructed of different diameter, depth, and wall thickness than other reagent chambers. For example, a reaction chamber preferably will be a thin-walled chamber to aid in thermal conduction between external thermocyclers located in the base unit and the fluid within the reaction chamber. The walls should be tapered so as to easily fit into the thermocycler and make thermal contact with thermocycler without adhering to its surface. The reaction chamber should be of a depth and shape that allows for its fluid volume to be positioned inside the thermocycler. The depth of the PCR chamber should be compatible with the vertical motion of the cassette pipette. Preferably, the chamber will also be accessible to a user's pipette tip if inserted into the chamber through the casette's fill port 14 and the material used to form the PCR chamber may be optically clear so that the user can see when the pipette tip has reached the bottom of the chamber.

Disadvantages have been found in both real-time PCR, which pairs amplification and detection, and multiplex-PCR, which generally is performed as an amplification step followed by a separate detection procedure. Use of a single reaction tube has been an attractive option because it offers the opportunity to limit contamination. However, this also limits the user's ability to perform a more sensitive and quantitative or semi-quantitative analysis of a specimen. The present disclosure provides an automated method for performing multiplex-PCR in combination with detection, decreasing the possibility of contamination during the process. The ARM-PCR procedure provided by the combination of the cassette described herein and the two-amplification-step, two-primer set protocol of ARM-PCR, provides highly sensitive, highly-specific, semi-quantitative amplification and detection of multiple targets (e.g., 20, 30, 40, etc.) without the risk of contamination of either the amplification reactions or the detection hybridization procedure. Cassettes are single-use, disposable cassettes and may be loaded with primers needed to detect the presence of multiple different targets such as a variety of bacteria, fungi, viruses, etc. Cassettes may be provided to users in hospital and clinic laboratories, for example, to quickly screen a clinical sample to detect the presence of agents which may cause respiratory, gastrointestinal, or other disease. The disclosure may be further described by means of the following non-limiting examples:

EXAMPLE

A user opens the filler cap on the cassette and inserts a pipette tip into the cassette through the filler port to deposit a 5 microliter sample into the PCR chamber. The pipette is then withdrawn and the filler cap is sealed. The cassette is snapped into the base unit.

Installation of the cassette contacts the cassette parts with the cam bar rotational interface, the pump push rod linear motion interface, and the lead screw rotational interface. The detector cover door latch is tripped, releasing the cover door (if utilized) so it can slide out of the way, exposing the cassette's microarray to the base unit. When the base unit detects the cassette, it automatically reads a barcode label on the cassette. The base unit will verify that the correct cassette has been loaded for the type of test to be performed. The base unit then engages the heater units for the PCR thermal cycler and the optical/heater for hybridization and detection. The heaters are moved upward by the base unit to make thermal contact with the bottom of the PCR chamber and the detection chamber of the cassette.

The ARM protocol comprises two series of PCR steps, which are designated below according to the series and the step number:

PCR1-1. The base unit machine's optical or magnetic sensors verify the pipette position.

PCR1-2. The pump push rod is pressed displacing air out of the pipette tip.

PCR1-3. The cam bar rotates and lowers the pipette.

PCR1-4. The pipette pierces the foil seal above PCR1 reagent chamber.

PCR1-5. The pipette continues down into the reagent chamber.

PCR1-6. The pump push rod is released.

PCR1-7. Fluid enters the pipette tip.

PCR1-8. The cam bar rotates back to home position.

PCR1-9. The pipette spring raises the pipette tip out of the reagent chamber.

PCR1-10. The lead screw is rotated and the pipette is moved into position over the PCR chamber.

PCR1-11. The base unit machine's optical or magnetic sensors verify the motion.

PCR1-12. The cam bar rotates and lowers the pipette to the bottom of the PCR chamber.

PCR1-13. The pump push rod is pressed displacing the fluid out of the pipette tip and into the chamber.

PCR1-14. The cam bar rotates back to home position.

PCR1-15. The pipette spring raises the pipette tip out of the PCR chamber.

PCR1-16. The lead screw is rotated and the pipette is moved over the mineral oil reagent chamber.

PCR1-17. The base unit machine's magnetic sensors verify the motion.

PCR1-18. The cam bar rotates and lowers the pipette.

PCR1-19. The pipette pierces the foil seal above the mineral oil reagent chamber.

PCR1-20. The pipette continues down into the reagent chamber.

PCR1-21. The pump push rod is released.

PCR1-22. Fluid enters the pipette tip.

PCR1-23. The cam bar rotates back to home position.

PCR1-24. The pipette spring raises the pipette tip out of the reagent chamber.

PCR1-25. The lead screw is rotated and the pipette is moved over the PCR chamber.

The base unit machine's optical or magnetic sensors verify the motion.

PCR1-26. The cam bar rotates and lowers the pipette to the bottom of the PCR chamber.

PCR1-27. The pump push rod is pressed displacing the fluid out of the pipette tip and into the chamber.

PCR1-28. The cam bar rotates back to home position.

PCR1-29. The pipette spring raises the pipette tip out of the PCR chamber.

PCR1-30. The base unit performs all the PCR temperature cycles.

PCR1-31. The base unit machine holds the PCR chamber at 55 degrees centigrade

PCR1-32. The lead screw is rotated and the pipette is moved over the capture probe fluid well. The base unit machine's optical or magnetic sensors verify the motion.

PCR1-33. The cam bar rotates and lowers the pipette.

PCR1-34. The pipette pierces the foil seal above the capture probe reagent chamber and continues down into the reagent chamber.

PCR1-35. The pump push rod is released.

PCR1-36. Fluid enters the pipette tip.

PCR1-37. The cam bar rotates back to home position.

PCR1-38. The pipette spring raises the pipette tip out of the reagent chamber.

PCR1-39. The lead screw is rotated and the pipette is moved over the PCR chamber.

The base unit machine's optical or magnetic sensors verify the motion.

PCR1-40. The cam bar rotates and lowers the pipette to the bottom of the PCR chamber.

PCR1-41. The pump push rod is pressed displacing the fluid out of the pipette tip and into the chamber.

PCR1-42. The cam bar rotates back to home position.

PCR1-43. The pipette spring raises the pipette tip out of the PCR chamber.

PCR1-44. The capture probe now captures the PCR product produced in the PCR1 reaction.

PCR1-45. The lead screw is rotated and the pipette is moved over the magnetic bead reagent chamber. The base unit machine's optical or magnetic sensors verify the motion.

PCR1-46. The cam bar rotates and lowers the pipette.

PCR1-47. The pipette pierces the foil seal above the magnetic bead reagent chamber.

PCR1-48. The pipette continues down into the fluid chamber.

PCR1-49. The pump push rod is released.

PCR1-50. Fluid enters the pipette tip.

PCR1-51. The cam bar rotates back to home position.

PCR1-52. The pipette spring raises the pipette tip out of the reagent chamber.

PCR1-53. The lead screw is rotated and the pipette is moved over the PCR chamber.

Magnetic sensors in the base unit verify the motion.

PCR1-54. The cam bar rotates and lowers the pipette to the bottom of the PCR chamber.

PCR1-55. The pump push rod is pressed displacing the fluid out of the pipette tip and into the chamber.

PCR1-56. The cam bar rotates back to home position.

PCR1-57. The pipette spring raises the pipette tip out of the PCR chamber.

PCR1-58. The base unit thermocycler raises the PCR chamber temperature to 80 degrees centigrade.

PCR1-59. The magnetic beads now capture the capture probe.

PCR1-60. The base unit moves a magnet to the bottom of the PCR chamber and the magnetic beads are drawn to the wall and held there.

PCR1-61. The cam bar rotates and lowers the pipette into the PCR chamber.

PCR1-62. The pump push rod is released.

PCR1-63. Fluid enters the pipette tip. The magnetic beads stay on the sidewall of the chamber.

PCR1-64. The cam bar rotates back to home position.

PCR1-65. The pipette spring raises the pipette tip out of the reagent chamber.

PCR1-66. The lead screw is rotated and the pipette is moved over a waste chamber.

The base unit's optical or magnetic sensors verify the motion.

PCR1-67. The cam bar rotates and lowers the pipette to the bottom of the waste chamber.

PCR1-68. The pump push rod is pressed displacing the fluid out of the pipette tip and into the chamber.

PCR1-69. The cam bar rotates back to home position.

PCR1-70. The pipette spring raises the pipette tip out of the chamber.

PCR1-71. The lead screw is rotated and the pipette is moved over the PCR 2 reagent fluid well. The base unit machine's magnetic sensors verify the motion.

PCR1-72. The cam bar rotates and lowers the pipette.

PCR1-73. The pipette pierces the foil seal above the PCR 2 reagent fluid well.

PCR1-74. The pipette continues down into the fluid chamber.

PCR1-75. The pump push rod is released.

PCR1-76. Fluid enters the pipette tip.

PCR1-77. The cam bar rotates back to home position.

PCR1-78. The pipette spring raises the pipette tip out of the fluid well holding the fluid inside.

PCR1-79. The lead screw is rotated and the pipette is moved over the PCR chamber.

The base unit machine's magnetic sensors verify the motion.

PCR1-80. The cam bar rotates and lowers the pipette to the bottom of the PCR chamber.

PCR1-81. The pump push rod is pressed displacing the fluid out of the pipette tip and into the chamber.

PCR1-82. The cam bar rotates back to home position.

PCR1-83. The pipette spring raises the pipette tip out of the PCR chamber and the base unit is ready to perform PCR 2.

The second PCR series amplifies the amplicon from PCR 1, the amplicon from PCR 1 having been rescued using magnetic beads held to the sidewall of the PCR chamber.

PCR2-1. The base unit removes the magnet from the chamber sidewall.

PCR2-2. The base unit performs 3 PCR cycles with the beads free to move in solution.

PCR2-3. The rescued DNA held to the beads is dropped off during these three cycles.

PCR2-4. The base unit machine now brings the magnet back to the sidewall.

PCR2-5. The magnetic beads are drawn to the wall and are held there.

PCR2-6. The base unit machine completes the rest of the PCR cycles.

PCR2-7. The lead screw is rotated and the pipette is moved over the hybridization fluid well. The base unit machine's magnetic sensors verify the motion.

PCR2-8. The cam bar rotates and lowers the pipette.

PCR2-9. The pipette pierces the foil seal above the hybridization fluid well.

PCR2-10. The pipette continues down into the fluid chamber.

PCR2-11. The pump push rod is released.

PCR2-12. Fluid enters the pipette tip.

PCR2-13. The cam bar rotates back to home position.

PCR2-14. The pipette spring raises the pipette tip out of the fluid well holding the fluid inside.

PCR2-15. The lead screw is rotated and the pipette is moved over the detector chamber.

The base unit machine's magnetic sensors verify the motion.

PCR2-16. The cam bar rotates and lowers the pipette into the detection chamber.

PCR2-17. The pump push rod is pressed displacing the fluid out of the pipette tip and into the chamber.

PCR2-18. The cam bar rotates back to home position.

PCR2-19. The pipette spring raises the pipette tip out of the chamber.

PCR2-20. The base unit machine begins heating the detection chamber to 55 degrees centigrade.

PCR2-21. The lead screw is rotated and the pipette is moved over the PCR chamber. The base unit machine's magnetic sensors verify the motion.

PCR2-22. The cam bar rotates and lowers the pipette into the PCR chamber.

PCR2-23. The pump push rod is released.

PCR2-24. Fluid enters the pipette tip.

PCR2-25. The cam bar rotates back to home position.

PCR2-26. The pipette spring raises the pipette tip out of the fluid well holding the fluid inside.

PCR2-27. The lead screw is rotated and the pipette is moved over the detector chamber.

The base unit machine's magnetic sensors verify the motion.

PCR2-28. The cam bar rotates and lowers the pipette into the detection chamber.

PCR2-29. The pump push rod is pressed displacing the fluid out of the pipette tip and into the chamber.

PCR2-30. The cam bar rotates back to home position.

PCR2-31. The pipette spring raises the pipette tip out of the chamber.

PCR2-32. The base unit machine holds the detection chamber at 55 degrees centigrade and lets the hybridization to the microarray take place.

PCR2-33. The cam bar rotates and lowers the pipette into the detection chamber.

PCR2-34. The pump push rod is released.

PCR2-35. Fluid enters the pipette tip.

PCR2-36. The cam bar rotates back to home position.

PCR2-37. The pipette spring raises the pipette tip out of the fluid well holding the fluid inside.

PCR2-38. The lead screw is rotated and the pipette is moved over the waste chamber. The base unit machine's magnetic sensors verify the motion.

PCR2-39. The cam bar rotates and lowers the pipette into the waste chamber.

PCR2-40. The pump push rod is pressed displacing the fluid out of the pipette tip and into the waste chamber.

PCR2-41. The cam bar rotates back to home position.

PCR2-42. The pipette spring raises the pipette tip out of the chamber.

PCR2-43. The lead screw is rotated and the pipette is moved over the washing fluid well.

The base unit machine's magnetic sensors verify the motion.

PCR2-44. The cam bar rotates and lowers the pipette.

PCR2-45. The pipette pierces the foil seal above the washing fluid well.

PCR2-46. The pipette continues down into the fluid chamber.

PCR2-47. The pump push rod is released.

PCR2-48. Fluid enters the pipette tip.

PCR2-49. The cam bar rotates back to home position.

PCR2-50. The pipette spring raises the pipette tip out of the fluid well holding the fluid inside.

PCR2-51. The lead screw is rotated and the pipette is moved over the detector chamber.

The base unit machine's magnetic sensors verify the motion.

PCR2-52. The cam bar rotates and lowers the pipette into the detection chamber. PCR2-53. The pump push rod is pressed displacing the fluid out of the pipette tip and into the chamber.

PCR2-54. The cam bar rotates back to home position.

PCR2-55. The pipette spring raises the pipette tip out of the chamber.

PCR2-56. The cam bar rotates and lowers the pipette into the detection chamber.

PCR2-57. The pump push rod is released.

PCR2-58. Fluid enters the pipette tip.

PCR2-59. The cam bar rotates back to home position.

PCR2-60. The pipette spring raises the pipette tip out of the fluid well holding the fluid inside.

PCR2-61. The lead screw is rotated and the pipette is moved over the waste chamber. The base unit machine's magnetic sensors verify the motion.

PCR2-62. The cam bar rotates and lowers the pipette into the waste chamber.

PCR2-63. The pump push rod is pressed displacing the fluid out of the pipette tip and into the waste chamber.

PCR2-64. The cam bar rotates back to home position.

PCR2-65. The pipette spring raises the pipette tip out of the chamber.

PCR2-66. The lead screw is rotated and the pipette is moved over the washing fluid well.

The base unit machine's magnetic sensors verify the motion.

PCR2-67. The cam bar rotates and lowers the pipette.

PCR2-68. The pipette continues down into the fluid chamber.

PCR2-69. The pump push rod is released.

PCR2-70. Fluid enters the pipette tip.

PCR2-71. The cam bar rotates back to home position.

PCR2-72. The pipette spring raises the pipette tip out of the fluid well holding the fluid inside.

PCR2-73. The lead screw is rotated and the pipette is moved over the detector chamber.

The base unit machine's magnetic sensors verify the motion.

PCR2-74. The cam bar rotates and lowers the pipette into the detection chamber.

PCR2-75. The pump push rod is pressed displacing the fluid out of the pipette tip and into the chamber.

PCR2-76. The cam bar rotates back to home position.

PCR2-77. The pipette spring raises the pipette tip out of the chamber.

Certain steps may be performed an additional two or more times, washing the detector array and removing non hybridized DNA which would show up as a background reading in the detector.

As described above and shown in the associated drawings, the present disclosure describes an apparatus for performing amplicon rescue multiplex PCR. While particular embodiments of the disclosure have been described, it will be understood, however, that the disclosure is not limited thereto, since modifications may be made by those skilled in the art, particularly in light of the foregoing teachings. It is, therefore, contemplated by the appended claims to cover any such modifications that incorporate those features or those improvements that embody the spirit and scope of the present disclosure.

What is claimed is:

1. A cassette for amplification and detection of nucleic acids, comprising:
    a base having a plurality of chambers; and
    a pipette positioned within a cavity of the cassette and moveably connected to a portion of the cassette such that the pipette is moveable vertically and horizontally within the cavity for selectively positioning the pipette within each of the plurality of chambers.

2. The cassette of claim 1 further comprising a cam bar rotatably connected to a portion of the cassette wherein rotation of the cam bar moves the pipette into and out of the plurality of chambers.

3. The cassette of claim 1 further comprising a lead screw rotatably connected to a portion of the cassette wherein rotation of the lead screw moves the pipette horizontally within the cavity.

4. The cassette of claim 1 further comprising a pipette pump assembly wherein activation of the pump assembly creates a vacuum within the pipette.

5. The cassette of claim 1 wherein the cassette has a fill port.

6. The cassette of claim 5 further comprising a fill port cap for the fill port.

7. The cassette of claim 6 further comprising a door slidably coupled to the cassette for selectively covering the fill port cap.

8. A cassette for amplification and detection of nucleic acids, comprising:
 a pipette holder positioned within a cavity of the cassette and movable vertically and horizontally within the cavity;
 a pipette connected to the pipette holder;
 a cam bar rotatably connected to a portion of the cassette wherein rotation of the cam bar moves the pipette into and out of a chamber of a base of the cassette;
 a lead screw rotatably connected to a portion of the cassette wherein rotation of the lead screw moves the pipette holder within the cavity; and
 a pipette pump assembly wherein activation of the pump assembly creates a vacuum within the pipette.

9. The cassette of claim 8 further comprising a tube connecting the pipette pump assembly to the pipette.

10. The cassette of claim 9 wherein the tube further comprises a spiral wrap.

11. The cassette of claim 8 wherein the cassette has a fill port.

12. The cassette of claim 11 further comprising a fill port cap for the fill port.

13. The cassette of claim 12, further comprising a door slidably coupled to the cassette for selectively covering the fill port cap.

14. A cassette for the amplification and detection of nucleic acids, the cassette comprising:
 a pipette holder;
 a pipette seated within the pipette holder; and
 means for adjusting horizontal and vertical displacement of the pipette and the pipette holder within a cavity of the cassette for selectively positioning the pipette within each of a plurality of chambers of the cassette.

15. The cassette of claim 1, wherein the cavity is closed.

16. The cassette of claim 8, wherein the cavity is closed.

17. The cassette of claim 14, wherein the cavity is closed.

* * * * *